United States Patent [19]

Gammans

[11] Patent Number: 5,116,852
[45] Date of Patent: May 26, 1992

[54] TREATMENT OF SLEEP DISORDERS

[75] Inventor: Richard Gammans, Killingworth, Conn.

[73] Assignee: Bristol-Myers Squibb Co., New York, N.Y.

[21] Appl. No.: 620,696

[22] Filed: Dec. 3, 1990

[51] Int. Cl.⁵ .............................................. A61K 31/41
[52] U.S. Cl. .................................................. 514/359
[58] Field of Search ......................................... 514/359

[56] References Cited

U.S. PATENT DOCUMENTS 4,338,317  7/1982  Temple et al. ....................... 544/366

OTHER PUBLICATIONS

Bramanti et al., Prog. Neuro-Psych. & Biol. Psychiat., 1985, vol. 9, pp. 157–165.
Di Perri et al., Prog. Neuro-Psycho Psycho. & Biol. Psychiat. 1986, vol. 11, pp. 65–70.
Soldatos et al., Prog. Neuro-Psycho. & Biol. Psychiat 1988, vol. 12, pp. 899–907.
Nicholson et al., Drugs 38 (Suppl 1): 4–13 (1989).
Prinz et al., New England Jounal. of Med., vol. 323, No. 8, (1990), pp. 520–526.
ASDA, The International Classification of Sleep Disorders: Diagnostic & Coding Manual, (1990), pp. 297–313.

*Primary Examiner*—S. J. Friedman
*Attorney, Agent, or Firm*—Sandra M. Nolan

[57] ABSTRACT

Certain antidepressants have been found to alleviate sleeping disorders associated with less than normal REM sleep.

4 Claims, No Drawings

TREATMENT OF SLEEP DISORDERS

BACKGROUND

Several sleep disorders, such as dysomnia, sleep walking disorders, jet-lag and certain emotionally-, drug- or age-related sleep disturbances, can be alleviated if the patient, or subject, suffering therefrom can be induced to engage in paradoxical or rapid eye movement (REM) sleep for longer periods of time.

Unfortunately, the use of the majority of known drugs, e.g., trazodone and other 5HT-2 antagonists, benzodiazepine sedatives, barbiturates and the like, which have been given to help persons afflicted with these types of disturbances, have generally resulted in the person's having shorter REM sleep periods or less deep REM sleep, delayed the first REM episode, i.e., increased REM latency, and reduced the number of discrete REM episodes experienced during the night.

REM sleep is believed to be important in the body's overall well being, since it is during periods of REM sleep that much of the damage done to the body as the result of physiological and/or psychological stress is repaired or alleviated.

The problem is exacerbated by the fact that abrupt withdrawal from most anti-depressants or sedatives usually induces "REM rebound", which can be associated with increased dream intensity and the occurrence of nightmares. The chapter entitled "Sleep Disorders" at pages 297-313 in *The International Classification of Sleep Disorders: Diagnostic and Coding Manual* published by the American Sleep Disorders Association (Rochester, Minn., 1990) discusses the rebounding effect as it manifests itself when antidepressants are withdrawn after treatment for dream anxiety disorder or nightmare disorder (page 308).

Sedative and hypnotic drugs, such as the benzodiazepines, are generally contraindicated since they actually decrease REM sleep time, prolong REM latency and produce REM rebound. Thus, with few exceptions, antidepressants have not been selected as agents when the object of treatment is the production of more deep, or REM, sleep and less light sleep.

Two studies discuss the use of amineptine, a tricyclic compound, to treat depression. Some discussion of the drug's effects on sleep cycles is also presented. See P. Bramanti et al, "Study of the Hypnic Effect of Amineptine Evaluation by Means of Polygraphy and Tests", *Prog Neuro-Psychopharmacol. & Biol. Psychiat.*, 1985, vol. 9, pp. 157-65 (Pergamon Press Ltd, 1985) and R. Di Perri, et al, "The Effects of Amineptine on the Mood and Nocturnal Sleep of Depressed Patients", *Prog. Neuro-psychopharmacol. & Biol. Psychiat.* 1987, vol. 11, pp. 65-70 (Pergamon Journals Ltd., 1987).

In another study, C. Soldatos et al. reported that an experimental tricyclic antidepressant, designated "S-3344", increases REM sleep. See *Prog. Neuro. Psychopharmacol. & Biol. Psychiat.*, 1988, vol. 12, pp. 899-907 (Pergamon Press, 1988).

THE INVENTION

It has been discovered that certain compounds, and their pharmaceutically acceptable derivatives, are effective in treating sleep disorders because of their propensity to increase both the duration and occurrence of REM sleep.

Disorders which may be treated using the process of the invention include a variety of conditions which are usually associated with decreased REM sleep, decreased slow-wave (i.e., state 3 or 4) sleep, or both. Among them are nocturnal myoclonus, REM sleep interruptions, jet-lag, shift workers' sleep disturbances, dysomnias, night terror, sleep walking, insomnias associated with depression and those associated with other emotional/mood disorders.

In addition, certain drugs may also cause reductions in REM sleep as a side effect. The process of the invention may be used to correct those types of sleeping disorders as well.

The compounds useful herein are those of Formula I and their derivatives. Formula I is:

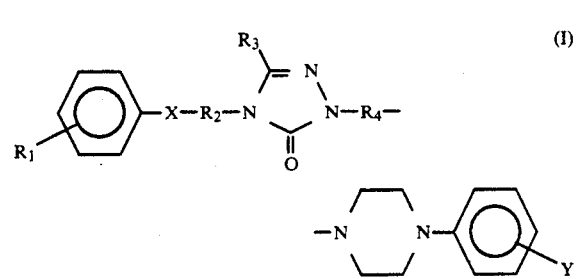

wherein
X is a direct bound, O, N, NH or S;
$R_1$ and $R_3$ are each hydrogen or $C_{1-6}$ substituted or unsubstituted hydrocarbon groups which may be connected to the ring via an -O- or -N- linkage;
$R_2$ and $R_4$ are each a direct bond, a $C_{1-8}$ saturated or an unsaturated hydrocarbon group;
Y is a halogen atom.

In a preferred embodiment, the compound nefazodone, a non-sedating antidepressant which has formula II,

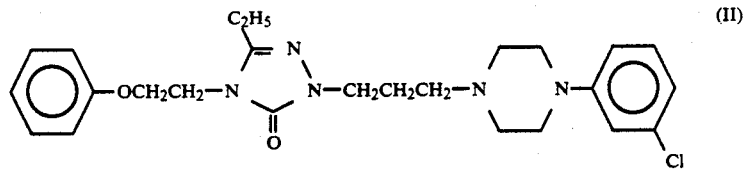

significantly increased REM sleep in clinical tests conducted in human volunteers. Nefazodone also yielded decreases in REM latency (i.e., the sleeping time before REM phases begin), while maintaining a normal duration of slow-wave sleep.

Nefazodone is the subject of U.S. Pat. No. 4,338,317, which shows its production and use as an antidepressant. Several of its salts are also disclosed.

OBJECTS OF THE INVENTION

The invention deals with a method for treating sleep disorders via the administration of suitable quantities of compounds of formula I.

In addition, it deals with enhancing REM sleep in patients, so that the alleviation of certain forms of insomnia, which are associated with REM sleep periods of abnormally short duration, delayed onset of REM sleep or reduced number of REM episodes, is attained.

ADVANTAGES

The process of the invention has several advantages over other methods of enhancing or inducing REM sleep in subjects suffering from sleep disorders.

The compounds of the invention are not sedatives. Thus, they do not cause daytime drowsiness or promote sleepiness or generally lengthen the duration of total sleep time (i.e., the combined time for REM and NREM, or non rapid eye movement, sleep).

In addition, while they are antidepressants, the drugs described herein do not shorten or suppress REM sleep time. Thus, REM sleep, which is beneficial in assisting the body in its attempts to alleviate the effects of various stresses, is maximized. Heretofore, all known marketed antidepressants have reduced REM, prolonged REM latency and reduced the number of REM episodes which occurs.

Also, because the compounds of the invention are antidepressants, they tend to make the subjects using them feel better during their waking hours.

These and other advantages will be apparent after a consideration of the following description and claims.

DESCRIPTION OF THE INVENTION

The Compounds

The compounds, or drugs, which are the active ingredients in the processes of the invention are compounds of Formula I or their pharmaceutically acceptable derivatives. Formula I is:

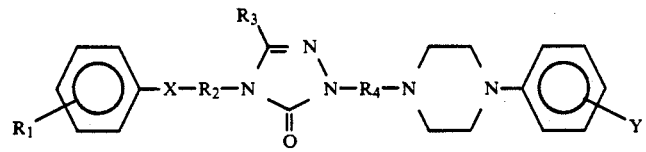

wherein

X is a direct bound, O, N, NH or S;

$R_1$ and $R_3$ are each hydrogen or $C_{1-6}$ substituted or unsubstituted hydrocarbon groups which may be connected to the ring via an -O- or -N-linkage;

$R_2$ and $R_4$ are each a direct bond, a $C_{1-8}$ saturated or unsaturated hydrocarbon group;

Y is a halogen atom.

Mixtures of one or more compounds of Formula I and/or derivatives thereof, may be employed.

X may be a direct link, -O- =N-, -NH- or -S-. Preferably, X is -O- or -S-, with -O- most preferred.

$R_1$ and $R_3$ are $C_{1-6}$ hydrocarbon groups or substituted $C_{1-6}$ groups having 0 to 2 sites of unsaturation. While it is preferred that they be hydrocarbon groups and preferably alkyl groups, one or both of $R_1$ and $R_3$ may have up to 3 substituents. In addition, $R_1$ and $R_3$ may contain -O-, -c(O) or -N- linkages. Useful substituent groups on $R_1$ and/or $R_3$ are Cl, Br, $NO_2$, $NH_2$, $PO_4$, and the like. When they are linked to their ring(s) via atoms, $R_1$ and/or $R_3$ may also be $-OR_4$, $-NHR_4$, $-C(O)R_4$ and $-C(O)OR_4$, wherein $R_4$ is a $C_{1-6}$ hydrocarbon group containing 0 to 2 sites of unsaturation.

It is preferred, however, that $R_1$ and $R_3$ be a H and a $C_{1-3}$ alkyl group respectively. It is highly preferred that $R_1$ be H and $R_3$ be $C_2H_5$.

$R_2$ and $R_4$ may each be a direct linkage or a $C_{1-8}$ hydrocarbon group. While the hydrocarbon group may have 1 or 2 sites of unsaturation, it is preferred that it have none, so that $R_2$ and $R_4$ are both saturated. Preferably $R_2$ and $R_4$ are $C_{2-5}$ alkylene bridges. Most preferably, $R_2$ is $C_2H_4$ and $R_4$ is $C_3H_6$, both aliphatic.

Y may be Cl, Br, Formula I, but is preferably Cl or Br, and most preferably Cl.

Pharmaceutically acceptable derivatives of compounds of Formula I include salts, esters, and the like. Useful salts can be be formed using such acids as hydrochloric, hydrobromic, hydroiodic, citric, acetic, benzoic, mondelic, phosphoric, nitric, mucic, isethionic, palmitic, heptmoic and the likes.

Preparation

The compounds of the invention are generally known compounds produced by conventional techniques. For example, nefazodone is produced by the procedures described in U.S. Pat. No. 4,338,317.

The preparation of other derivatives, such as the salts or esters is generally carried out by contacting the base with the acid or other suitable reactant. Such contact is preferably done while the reagents are in solution. Other conventional procedures for preparing derivatives are contemplated.

Dosages Levels

The compounds of the invention are to be administered in accordance with the needs of the particular patient and under the supervision of a competent physician. Generally, however, they are used in dosages of about 25 mg/day to about 1,500 mg/day, with administration of about 25 to about 600 mg/day preferred, and 100 to about 400 mg/day highly preferred.

The drug is generally given 1 to 3 times per day, so that the total daily dosage is within the range set out above.

Dosage Forms

While oral administration is preferred, the compounds of the invention may be administered via a variety of routes. Intravenous, intramuscular subcutaneous, transnasal, transdermol, ocular and rectal routes are also contemplated.

When transdermal, ocular or other topical delivery routes are employed, the drug(s) will be formulated into suitable formulations. Those formulations will contain conventional ingredients, eg, fillers, colorants, penetration enhancers, stabilizers, etc. in suitable quantities.

The following example illustrates the invention:

EXAMPLE

Unless otherwise stated, all percentages stated are weight percentages based on total composition weight; all times and percentages are rounded off to the nearest whole numbers.

In clinical studies performed on human subjects, 400 mg of nefazodone was administered orally to twelve (12) individuals. A control group of 12 was given a placebo. Two other groups of 11 and 12 subjects each, respectively, were given oral 200 mg trazodone and buspirone. Both of these drugs generally are considered sedating antidepressants.

The nefazodone group experienced an average of 116 minutes of REM or state 5 sleep, compared to 96 minutes of REM sleep for the placebo (in control) group. The trazodone and buspirone recipients averaged 67 and 70 minutes of REM sleep.

When one looks at the percentage of REM sleep time based on total sleep time, one can see that about 28% of the nefazodone group's total sleep was REM sleep while only 22% of the total sleep was REM sleep for the placebo recipients. The REM Sleep/Total Sleep percentages for trazodone and buspirone were 16% and 17%.

It was significant that the delta sleep, or phase 3 and 4 sleep values for the nefazodone group decreased slightly from 27 minutes (phase 3) and 28 minutes (phase 4) for the controls to 25 (both phases 3 and 4) for the nefazodone group.

Even more significant is the fact that both sleep latency and "light" sleep (i.e., stage 0, 1 and 2 sleep) decreased significantly.

Sleep latency, (time until sleep starts) dropped from the control group's 9 minutes, on average, to 5 minutes, on average, for the nefazodone group.

Light sleep was characterized in the control group by average times of 12 minutes (stage 0), 11 minutes (stage 1 and 267 minutes (stage 2). The nefazodone recipients had lower averages for light sleep, i.e., 15 minutes (stage 0), 9 minutes (stage 1) and 235 minutes (stage 2).

Total sleep time for the nefazodone group was 415 minutes, compared to total sleep times of 424 minute for the placebo group and 409 and 411 minutes total for the trazodone and buspirone groups.

It is clear that the nefazodone recipients—when compared to the control group—lost total sleep time (about 9 minutes), but gained in both delta sleep (deep, but not as deep as REM sleep) and REM (the deepest and most beneficial) sleep.

It is noteworthy, since total sleep time did not vary greatly, that most of the sleep time lost was lost in the light, or stage 0, 1 and 2, phases. Since the body is easily aroused from sleep during stages 0, 1 and 2, it is generally believed that this type of light sleep is less beneficial than the delta or REM types.

Note, too, that the trazodone and buspirone patients lost in both total sleep time (i.e., 409 and 410 minutes compared to nefazodone's total of about 415 and the controls 424) and that both of the traditionally "sedated" groups experienced only about 67 and 70 minutes of REM sleep, compared to the nefazodones REM average of about 116 minutes. Nefazodone represents an improvement, in terms of REM sleep, of 173% over trazodone and 165% over buspirone.

In addition, the nefazodone group's REM average of 116 minutes was 120% better than the placebo group's 96 minutes.

Reasonable variations, such as those which would occur to a skilled artisan, can be made herein without departing form the scope of the invention.

What is claimed is:

1. A method for the treatment of sleep disorders involving decreased REM sleep and/or decreased slow wave sleep, the method comprising administration to a subject in need thereof of a therapeutically effective regimen of at least one compound of Formula I:

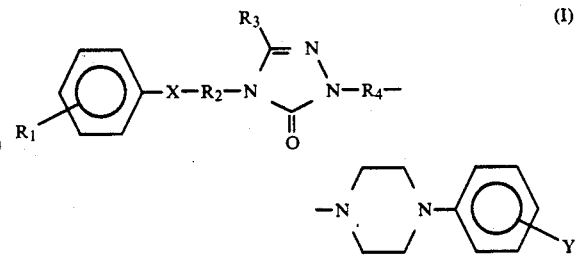

wherein
X is a direct bound, O, N, NH or S;
$R_1$ and $R_3$ are each hydrogen or $C_{1-6}$ substituted or unsubstituted hydrocarbon groups which may be connected to the ring via an -O- or -N- linkage;
$R_2$ and $R_4$ are each a direct bond, a $C_{1-8}$ saturated or an unsaturated hydrocarbon group;
Y is a halogen atom.

2. The method of claim 1 wherein the sleep disorder is selected from the group consisting of nocturnal myoclonus, REM sleep interruptions, jet-lag, shift workers sleep disturbances, dysomnias, night terrors, insomnias of depression, sleep walking disorders and other emotional/mood disorders.

3. The method of claim wherein the compound is nefazodone or a pharmaceutically acceptable derivative thereof.

4. The method of claim 3 wherein the compound is administered at a dosage level of about 25 mg/day to about 600 mg/day.